(12) United States Patent
Ichiki et al.

(10) Patent No.: US 10,385,305 B2
(45) Date of Patent: Aug. 20, 2019

(54) DEVICE FOR MEASURING ACTIVITY OF CULTURED CELLS, MICROCHAMBER AND METHOD OF MEASURING ACTIVITY OF CULTURED CELLS

(71) Applicants: THE UNIVERSITY OF TOKYO, Tokyo (JP); NIKON CORPORATION, Tokyo (JP)

(72) Inventors: Takanori Ichiki, Bunkyo-ku (JP); Hirofumi Shiono, Fujisawa (JP)

(73) Assignees: THE UNIVERSITY OF TOKYO, Tokyo (JP); NIKON CORPORATION, Tokyo (JP)

(*) Notice: Subject to any disclaimer, the term of this patent is extended or adjusted under 35 U.S.C. 154(b) by 0 days.

(21) Appl. No.: 14/642,265

(22) Filed: Mar. 9, 2015

(65) Prior Publication Data
US 2015/0225688 A1    Aug. 13, 2015

Related U.S. Application Data

(60) Division of application No. 12/964,094, filed on Dec. 9, 2010, now abandoned, which is a continuation of
(Continued)

(30) Foreign Application Priority Data

Jun. 26, 2008   (JP) ................................. 2008-167435

(51) Int. Cl.
*C12M 1/34*     (2006.01)
*C12Q 1/02*     (2006.01)
*G01N 33/50*    (2006.01)

(52) U.S. Cl.
CPC ............... *C12M 41/46* (2013.01); *C12Q 1/02* (2013.01); *G01N 33/5008* (2013.01)

(58) Field of Classification Search
CPC ...... C12M 41/46; C12Q 1/02; G01N 33/5008
(Continued)

(56) References Cited

U.S. PATENT DOCUMENTS 5,770,440 A    6/1998  Berndt
5,891,739 A    4/1999  Berndt
(Continued)

FOREIGN PATENT DOCUMENTS

JP    2004-81083 A    3/2004
JP    2004-81084 A    3/2004
(Continued)

OTHER PUBLICATIONS

Kamarck, M., "Fluorescence-Activated Cell Sorting of Hybrid and Transfected Cells," Methods in Enzymology, vol. 151, pp. 150-165, 1987.
(Continued)

*Primary Examiner* — Michael L Hobbs
(74) *Attorney, Agent, or Firm* — Oliff PLC

(57) ABSTRACT

A device for measuring activity of cultured cells includes a position detecting unit specifying a position of a cell to be measured, a microchamber controlling unit disposing in the culture container a microchamber which surrounds the cell and forms a measurement space, the measurement space being minute with respect to a volume of the culture container, and a measuring unit measuring environmental factors contained in the measurement space.

19 Claims, 7 Drawing Sheets

Related U.S. Application Data application No. PCT/JP2009/002952, filed on Jun. 26, 2009.

(58) Field of Classification Search
USPC .................................................. 435/287.3
See application file for complete search history.

(56) References Cited

U.S. PATENT DOCUMENTS

| | | | |
|---|---|---|---|
| 6,037,171 | A | 3/2000 | Larsson |
| 6,385,380 | B1 | 5/2002 | Friedrich et al. |
| 6,653,124 | B1 | 11/2003 | Freeman |
| 2002/0063067 | A1* | 5/2002 | Bech ................ G01N 33/48728 205/775 |
| 2003/0082605 | A1 | 5/2003 | Hodge |
| 2003/0124599 | A1* | 7/2003 | Chen .................... B01J 19/0046 506/39 |
| 2004/0121453 | A1* | 6/2004 | Rao ........................ C12M 23/12 435/287.3 |
| 2005/0090005 | A1* | 4/2005 | Kojima .................... C12Q 1/18 435/404 |
| 2005/0272039 | A1* | 12/2005 | Yasuda .................. C07H 21/00 435/6.12 |
| 2006/0051733 | A1 | 3/2006 | Lowe et al. |
| 2007/0059763 | A1 | 3/2007 | Okano et al. |
| 2007/0161106 | A1 | 7/2007 | Jervis et al. |
| 2007/0281322 | A1* | 12/2007 | Jaffe ........................ G01J 3/10 435/7.1 |

FOREIGN PATENT DOCUMENTS

| | | |
|---|---|---|
| JP | 2005-532060 A | 10/2005 |
| JP | 2006-115723 A | 5/2006 |

OTHER PUBLICATIONS

Jul. 28, 2009 International Search Report issued in International Application No. PCT/JP2009/002952.

Feb. 8, 2011 International Preliminary Report on Patentability issued in International Application No. PCT/JP2009/002952.

Shimizu et al., "Electrochemical Property of Collagen Production in Fibroblast," The Electrical Society of Japan, Proceedings of the 60th Conference, p. 84 (1D21), Mar. 18, 1993.

Feb. 4, 2014 Notice of Reasons for Rejection issued in Japanese Application No. 2010-517771.

* cited by examiner

DEVICE FOR MEASURING ACTIVITY OF CULTURED CELLS, MICROCHAMBER AND METHOD OF MEASURING ACTIVITY OF CULTURED CELLS

CROSS REFERENCE TO THE RELATED APPLICATIONS

This application is a divisional of U.S. patent application Ser. No. 12/964,094, filed Dec. 9, 2010, which is a continuation application of International Application No. PCT/JP2009/002952, filed on Jun. 26, 2009, designating the U.S., in which the International Application claims a priority date of Jun. 26, 2008, based on prior filed Japanese Patent Application No. 2008-167435, the entire contents of which are incorporated herein by reference.

BACKGROUND

1. Field

The present application relates to a device for measuring activity of cultured cells, and to peripheral technologies thereof.

2. Description of the Related Art

Technologies for measuring biological activity of cultured cells are fundamental technologies in broad fields including state-of-the-art medical field such as regenerative medicine, screening of pharmaceutical products, and the like. For example, there exists processes to multiply and differentiate cells in vitro in the field of regenerative medicine. In these processes, it is inevitable to measure biological activity of cultured cells in order to control success/failure of differentiation of cells, canceration of cells, and presence of infection.

On the other hand, among methods for measuring activity of cells which have been known publicly, there is measurement with a flow cell sorter as an example of a method for analyzing and then separating cells. In the flow cell sorter, cells after being subjected to fluorescence staining treatment are isolated in a droplet which is given an electric charge, and this droplet is dropped. Then, the direction of falling of the droplet is controlled by applying an electric field based on the presence of fluorescence in the cells in this droplet and the amount of scattering light, thereby allowing collection of the cells in a fractionating manner in plural containers (see, for example, Michael E. Kamarck, Methods in Enzymology, Vol. 151, pp. 150 to 165, (1987)).

Further, as a method for evaluating activity of a mass of cells, there are also known enzyme immunoassay (EIA) and fluoroimmunoassay (FIA), or ELISA combining both of them for performing high sensitivity analysis of substances in liquid.

DETAILED DESCRIPTION OF THE EMBODIMENTS

<Description of a Method for Measuring Activity of a First Embodiment>

Figure 1A:
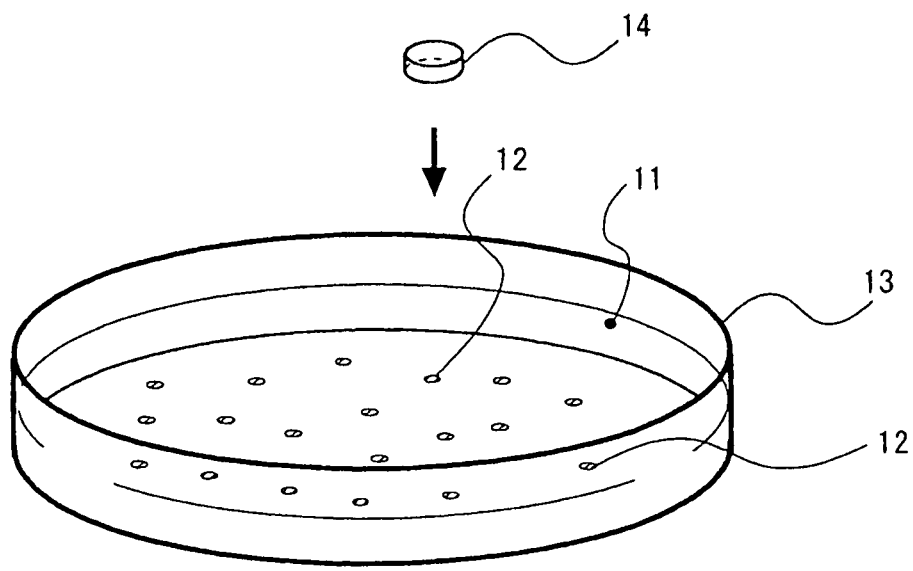
FIG. 1A, FIG. 1B are schematic views of a method for measuring activity according to one embodiment.
Figure 1B:
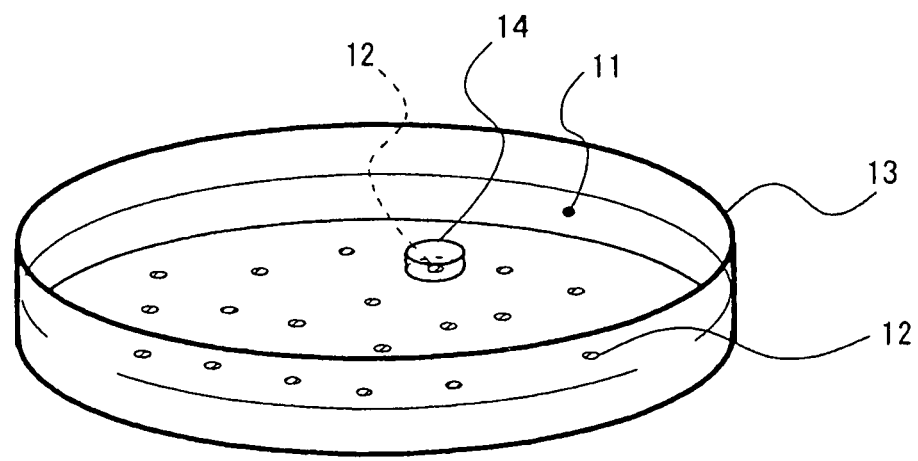

FIGS. 1A and 1B are views illustrating an overview of a method for measuring activity of cultured cells according to one embodiment. In one embodiment, in a culture container 13 such as a dish containing cultured cells 12 together with a liquid medium 11, a microchamber 14 surrounding a cell 12 to be measured is disposed, so as to measure environmental factors included in the space in the microchamber 14.

Here, the environmental factors in this specification mean substances produced or consumed through the process of metabolism in a cell. For example, the environmental factors include glucose, calcium ions, potassium ions, sodium ions, hydrogen ions, oxygen, reactive oxygen species, hydrogen peroxide, carbon dioxide, proteins and peptides produced by a cell (for example, cytokine, hormone, and the like), and so on.

Figure 2:
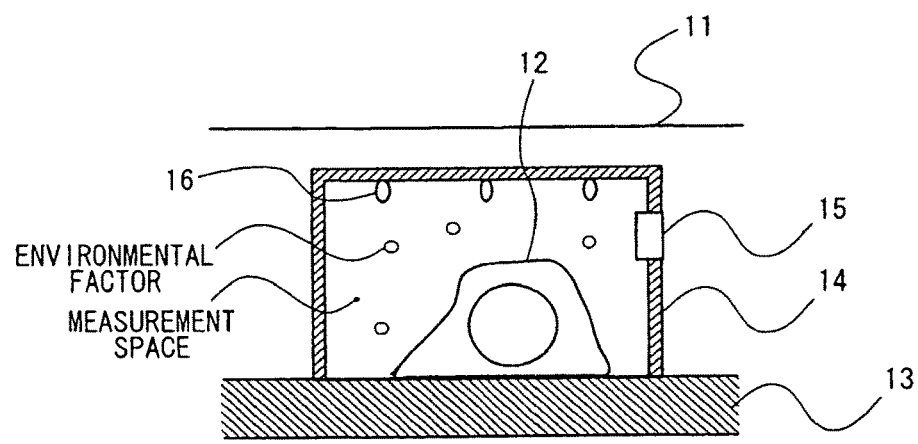
FIG. 2 is a cross-sectional view schematically illustrating a structure example of a microchamber according to one embodiment.

FIG. 2 is a cross-sectional view schematically illustrating a structure example of the microchamber 14 according to one embodiment. An overall shape of the microchamber 14 of one embodiment is formed as a bottomed cylindrical cup shape having an open bottom side to be in contact with a culture plane of the culture container 13 and a closed upper side. Accordingly, the cell 12 to be measured can be accommodated in the microchamber 14. In one embodiment, by disposing the microchamber 14 on the culture plane of the culture container 13, a measurement space which is sufficiently small with respect to the volume of the culture container 13 is built inside the microchamber 14. Here, the size of the microchamber 14 is selected appropriately according to the type and the number of cells 12 to be measured, the types of the environmental factors to be measured, and a required time for measurement, and so on. Here, the diameter of the chamber is set to about 50 μm to about 100 μm, for example.

Further, an environmental factor sensor 15 and biomolecule detecting probes 16 are fixed in the microchamber 14 of one embodiment. The environmental factor sensor 15 converts the amount of environmental factors contained in a culture solution into an electric signal by an electrochemical method. For example, the environmental factor sensor 15 is formed of an oxygen sensor and/or various bio-sensors (such as glucose sensor).

The biomolecule detecting probes 16 are formed of molecules which specifically acquire target molecules selected from the environmental factors, for which proteins such as antibodies and enzymes, peptides, saccharides, or the like can be used. In one embodiment, different kinds of biomolecule detecting probes 16 may be fixed in arrays at specific positions of the microchamber 14 (on an upper face or the like of the microchamber 14) by patterning or the like. In such a structure, exhaustive analysis of many items at the same time is possible. Further, when target molecules are marked by fluorescence, or the like, coupling between the biomolecule detecting probes 16 and the target molecules can be measured easily. In addition, in the above-described structure, the amount of target molecules can be measured also by fluorescence intensity.

Here, the microchamber 14 of one embodiment may have the following structures from (1) to (5) (or a combination of them).

(1) When the environmental factors are measured by optical measurement (fluorescence measurement, measurement of color changes, absorbance measurement), it is preferred that the microchamber 14 be formed of a translucent material passing light having the wavelength corresponding to an optical change which occurs in the microchamber 14. At this time in view of facilitating the optical measurement, it is preferred that the refractive index of the microchamber 14 be set to the same value as the refractive index of the liquid medium 11. Examples of materials having a translucency to visible light and a refractive index which is approximately equivalent to that of the liquid medium 11 include an amorphous fluororesin (for example, Cytop (registered trademark)), and the like.

Further, for performing the optical measurement, to avoid distortions in an optical image in the measurement, the upper face of the microchamber 14 may be flat. Alternatively, to improve NA in the optical measurement, a microlens may be formed on the upper face of the microchamber 14 (illustration of this is omitted).

(2) The microchamber 14 may be formed of an elastic material with high flexibility. With such a structure, for example, the microchamber 14 can be placed to cover the cell 12 to be measured without damaging an axial fiber, or the like connected to external cells. Further, when the microchamber 14 is slanted with respect to the culture plane of the culture container 13, errors in alignment can be absorbed by deformation of the microchamber 14. Here, an example of the elastic material used for the microchamber 14 is a silicone rubber (polydimethylsiloxane).

(3) The microchamber 14 may be formed of a material having an oxygen permeability. With such a structure, when measurement is performed for a relatively long time, an incubating environment of cells can be maintained in the microchamber 14. Of course, this structure is on the assumption that the concentration of oxygen is not included in items of measurement. Here, an example of an oxygen permeable material used for the microchamber 14 is a silicone rubber (polydimethylsiloxane).

(4) To facilitate filling of the measurement space with the liquid medium 11, hydrophilicity may be given to an inner surface of the microchamber 14 by forming a hydrophilic film, or the like. In this structure, when the liquid medium 11 is filled in the container in advance with the microchamber 14 being turned upside down so that air does not enter, and thereafter the microchamber 14 is returned to the original state (with the opening being on the bottom side), the liquid in the container is maintained by surface tension. Therefore, in this structure, the microchamber 14 filled with the liquid medium 11 in advance can be placed to cover the cells 12.

(5) On the surface of the microchamber 14, a film may be formed of a substance (polyethylene glycol (PEG), 2-methacryloyloxyethyl phosphorylcholine (MPC), or the like) which inhibits absorption of protein. In this structure, the influence of measurement to the incubating environment can be lowered.

Next, procedures of the method for measuring activity of cultured cells in one embodiment will be described specifically.

In a first procedure, the microchamber 14 is disposed so as to surround the cell 12 to be measured from an upper side in the culture container 13. Thus, the cell 12 to be measured is accommodated, and the measurement space which is minute with respect to the volume of the culture container 13 is formed inside the microchamber 14.

Further, to suppress adverse effects to the incubating environment by movement of heat, it is preferred that the microchamber 14 be kept warm at the same temperature as the medium 11. Here, there may be plural cells 12 to be accommodated in the measurement space, but in one embodiment, one cell is accommodated in the microchamber 14.

In a second procedure, the environmental factors contained in the measurement space are measured. Thus, it is possible to evaluate activity of the cell to be measured, the degree of apoptosis or differentiation of the cell, the nature of the cell, and so on based on the amount of the environmental factors measured.

When the environmental factors in the culture container 13 are measured, metabolites and the like scatter in the entire medium, and thus it is impossible to measure the environmental factors focusing on each individual cell. On the other hand, in one embodiment, the microchamber 14 is disposed in the culture container 13, and the minute measurement space including the cell 12 to be measured is formed, so as to measure the environmental factors. The environmental factors included in this measurement space relate closely to the cell 12 to be measured, and thus it is possible to measure local environmental factors focusing on the cell 12 to be measured under the incubating environment.

Further, since the measurement space in the microchamber 14 is minute with respect to the volume of the culture container 13, a change in concentration of metabolites or the like becomes large in the measurement space as compared to the environment outside the microchamber 14. Accordingly, the environmental factors can be detected with quite high sensitivity. Since a change in concentration of the environmental factors becomes large in the measurement space, it is possible to perform measurement in a relatively short time.

Moreover, in one embodiment, activity of the cell is evaluated with the environmental factors included in the space surrounding the cell 12 being the subject to be measured. Accordingly, the influence of measurement to the cell can be reduced as compared to when the cell itself is the subject to be measured. Further, in one embodiment, since the cell 12 to be measured can be measured as it is in the culture container 13, the influence to the cell 12 and the surrounding incubating environment by measurement can be reduced significantly.

Here, the measurement method in the second procedure will be described in more detail. Specifically, in the second procedure, the environmental factors in the measurement space are measured by the environmental factor sensor 15 disposed in the microchamber 14. Alternatively, in the second procedure, an optical change in the measurement space caused by the biomolecule detecting probes 16 disposed in the microchamber 14 or a reagent (such as pH indicator) may be observed with a microscope, so as to perform optical measurement of the environmental factors (such as fluorescence measurement, measurement of color changes, and absorbance measurement). In addition, the biomolecule detecting probes used in the aforementioned optical measurement may be one fixed to the inner surface of the microchamber 14, or one dropped directly in the medium 11 in the culture container 13 without being fixed to the microchamber 14.

Further, in the second procedure, to allow metabolites to accumulate sufficiently in the measurement space in the microchamber 14, the environmental factors may be measured when a predetermined standby time has passed after the measurement space is formed. Furthermore, in the second procedure, the environmental factors may be measured a plural number of times while respective measurement periods are varied. In this way, it becomes possible to obtain the rate of change of the amount of the environmental factors based on changes in the amount of the environmental factors and intervals of measurement.

In the third procedure, after the measurement of the environmental factors is finished, the microchamber 14 is removed from the culture container 13. Thus, the incubating environmental of cells can be recovered to almost the same state as that before the measurement. Therefore, in one embodiment, it is possible to periodically determine activity of the cell 12 incubated under the incubating environment in a substantially non-invasive manner by repeating from the first procedure to the third procedure described above.

In addition, in one embodiment, a plurality of microchambers 14 may be disposed in one culture container 13 to perform measurement of activity of different cells 12 in parallel.

Modification Example of One Embodiment

Figure 3:
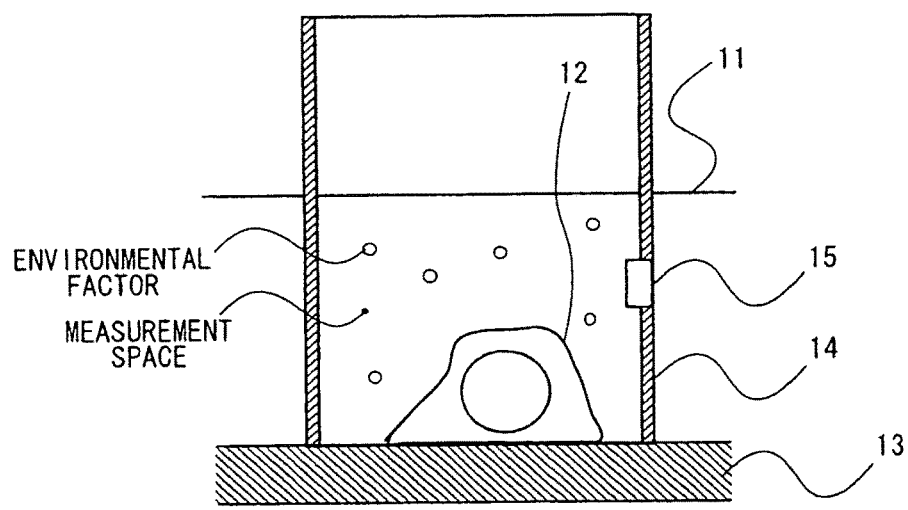
FIG. 3 is a cross-sectional view schematically illustrating another structure example of the microchamber.
Figure 4:
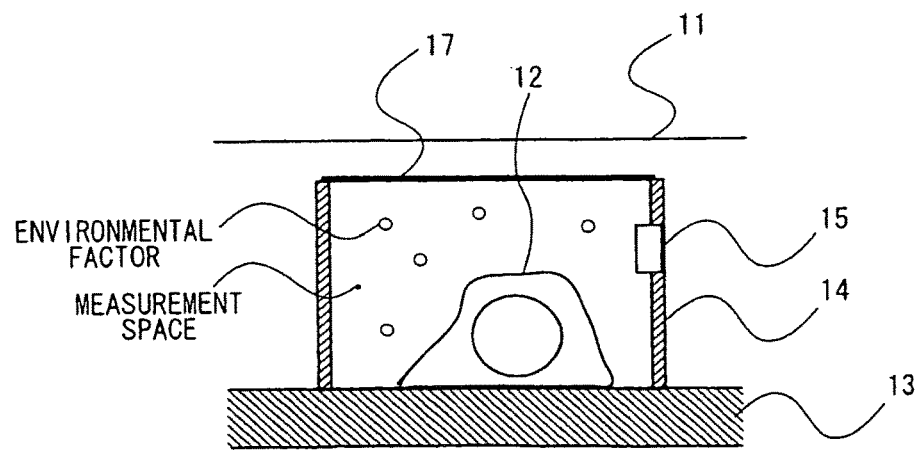
FIG. 4 is a cross-sectional view schematically illustrating another structure example of the microchamber.

FIG. 3 and FIG. 4 are cross-sectional views schematically illustrating other structure examples of the microchamber 14 of one embodiment. Also with these structures, a minute measurement space can be formed surrounding the cell 12 to be measured, and substantially the same effects as those of the microchamber 14 illustrated in FIG. 2 can be obtained. Note that in FIG. 3 and FIG. 4, components common to FIG. 2 are given the same reference numerals, and duplicated descriptions are omitted.

The microchamber 14 illustrated in FIG. 3 is formed of a cylindrical member in which both of a bottom face to be in contact with the culture container 13 and an upper face are open. With the structure in FIG. 3, air can be let out via the opening on the upper side when the microchamber 14 is place to cover the cell 12. In addition, in the structure of FIG. 3, the height of the microchamber 14 needs to be set so as to prevent flowing in of the medium 11 from the upper side of the microchamber 14.

The microchamber 14 illustrated in FIG. 4 is formed of a cylindrical member in which both of a bottom face to be in contact with the culture container 13 and an upper face are open. In the microchamber 14 of FIG. 4, an opening part on an upper side is covered with a hydrophobic semi-permeable film 17 which blocks the medium 11 flowing in or out and allows air to flow in or out. With the structure of FIG. 4, it is possible to let air out in one way via the opening on the upper side when the microchamber 14 is placed to cover the cell 12, and it is possible to prevent the medium 11 from mixing in and out of the microchamber 14 when the measurement space is formed.

<Description of a Method for Measuring Activity of Another Embodiment>

Figure 5A:
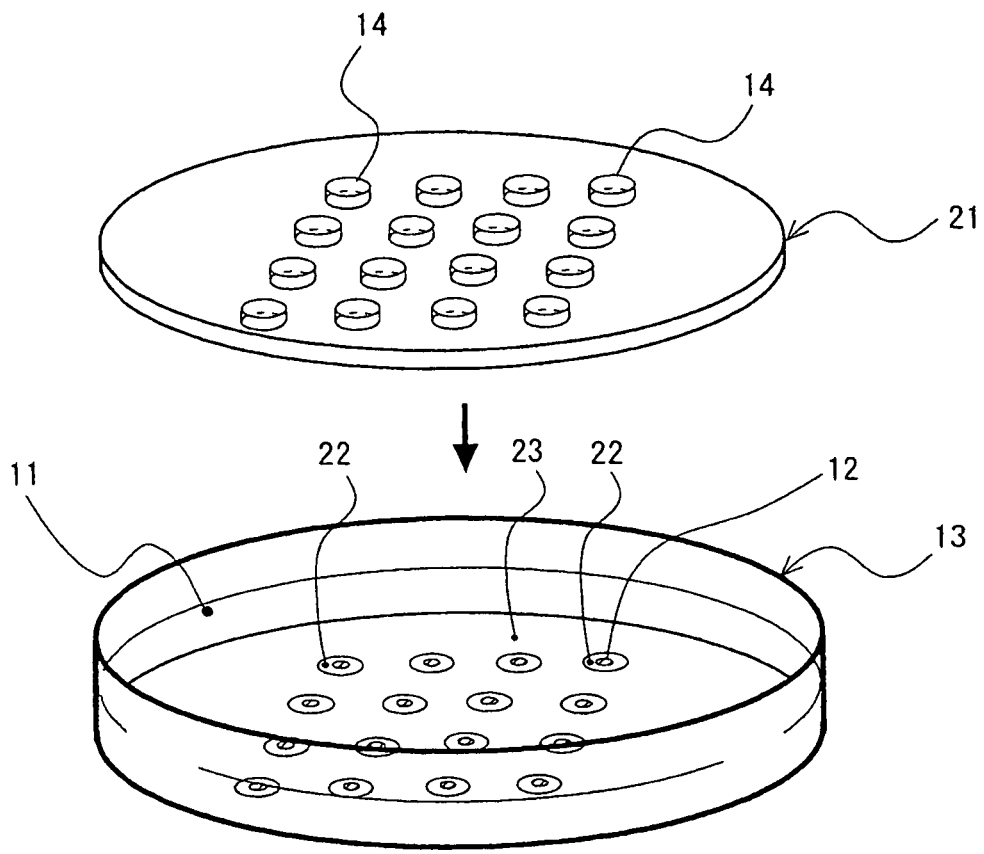
FIG. 5A, FIG. 5B are views schematically illustrating a method for measuring activity of cultured cells according to another embodiment.
Figure 5B:
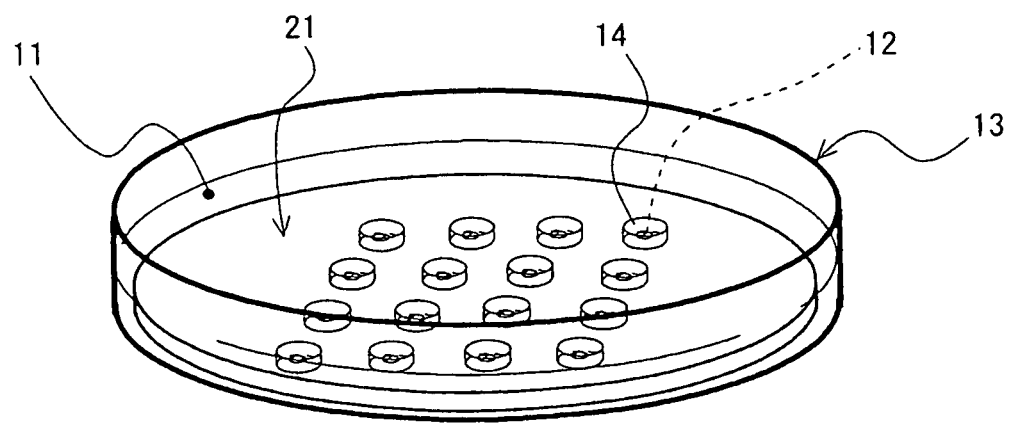

FIGS. 5A and 5B are views schematically illustrating a method for measuring activity of cultured cells according to another embodiment. The another embodiment is a modification example of the one embodiment illustrated in FIGS. 1A and 1B, in that measurement of the environmental factors is performed in each of measurement spaces using a microchamber sheet 21 having a sheet main body 24 in which microchambers 14 are arranged. In addition, in another embodiment, the culture plane on the side of the culture container 13 is modified to control adhering positions of cultured cells 12 to be aligned with the microchamber sheet 21.

Figure 6:
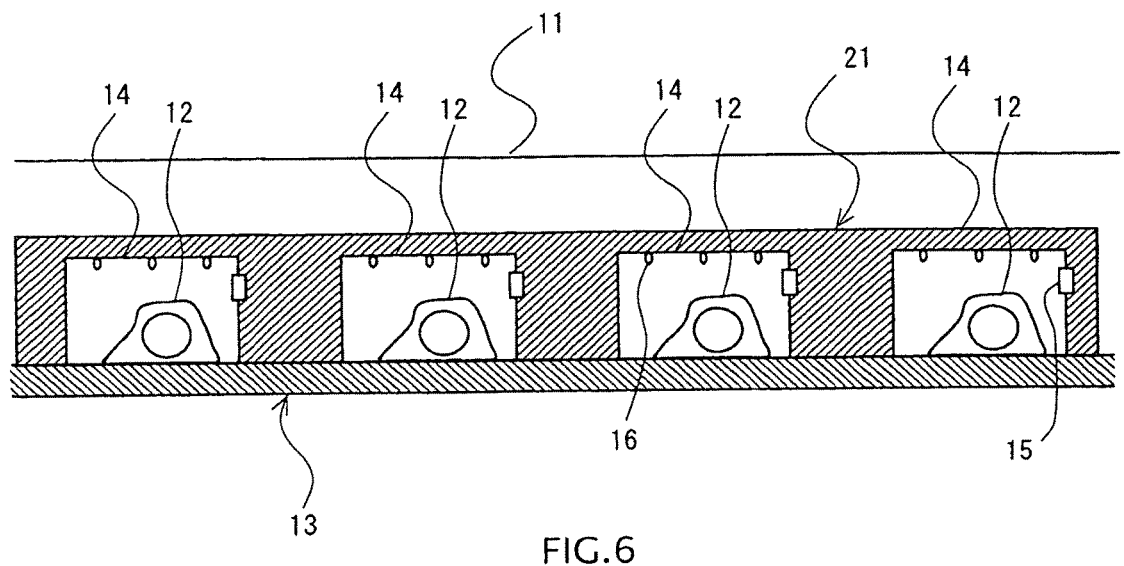
FIG. 6 is a partial cross-sectional view schematically illustrating a microchamber sheet according to another embodiment.
Figure 7:
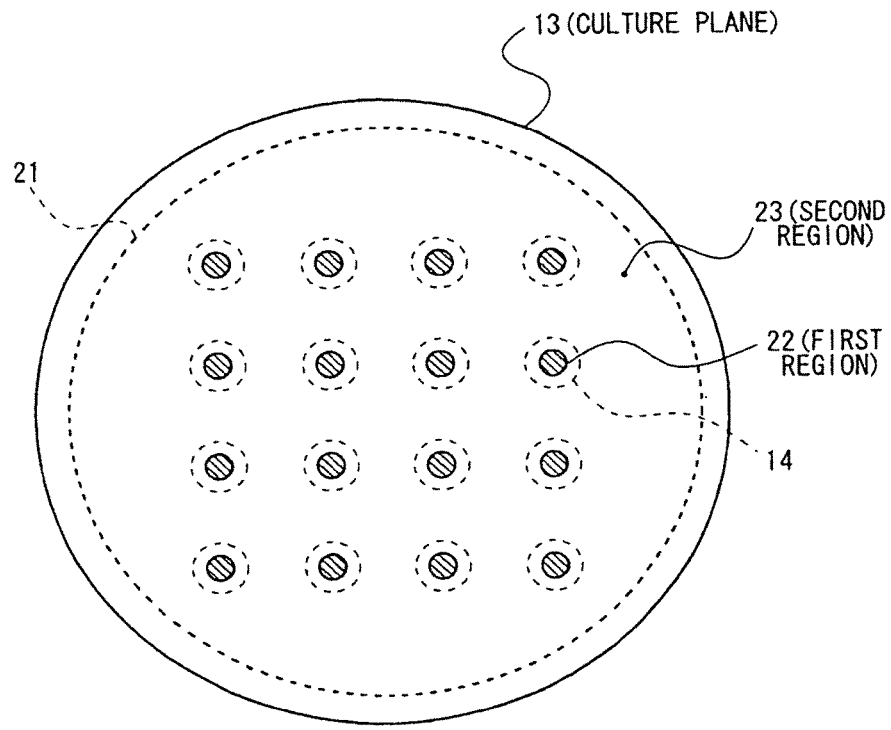
FIG. 7 is a view illustrating a correspondence between a culture plane of a culture container and the microchamber sheet used in another embodiment.

FIG. 6 is a partial cross-sectional view schematically illustrating the microchamber sheet 21 according to another embodiment. Further, FIG. 7 is a view illustrating a correspondence between the culture plane of the culture container 13 and the microchamber sheet 21 used in another embodiment. The overall shape of the microchamber sheet 21 according to another embodiment is a disc-like member with an outside diameter smaller than the inside diameter of the culture container 13, and a plurality of microchambers 14 are formed in one face (bottom side). The microchambers 14 are each formed of a cylindrical recessed portion with a bottom, and are formed by a publicly known microfabrication method, such as lithography, for example.

The respective microchambers 14 of the microchamber sheet 21 are arranged two-dimensionally at certain intervals. In FIGS. 5A, 5B and 7, for example, the microchamber sheet 21 with 4×4 arrays of microchambers 14 is illustrated.

On the other hand, on the culture plane of the culture container 13, first regions 22 and a second region 23 which have different adherences to cells are formed. The first regions 22 have a relatively high adherence to cells on the culture plane. A plurality of first regions 22 are formed on the culture plane, and the number of first regions corresponds to the number of microchambers 14 of the microchamber sheet 21. The first regions 22 on the culture plane form 4×4 arrays aligned with the intervals of the microchambers 14. Here, the size of each first region 22 is set to be slightly smaller than the size of the microchambers 14.

The second region 23 has a relatively low adherence to cells on the culture plane, and is formed to surround the first regions 22. Accordingly, in the culture container 13, cells adhere easily to the first regions 22 corresponding to the positions of the microchambers 14.

Here, as methods for forming the first regions 22 and the second region 23, the following examples (1) to (4) are conceivable. Note that these structures may be combined appropriately (1) Hydrophilicity is given to the first regions 22 to increase absorption of protein, making the adherence to cells in the first regions 22 relatively high. For example, the first regions 22 with hydrophilicity can be formed by patterning by irradiating the culture plane of the culture container 13 with plasma or ultraviolet rays.

(2) A polymeric film having an electric charge (for example, a coating of polylysine) is formed on the first regions 22 to increase absorption of protein, making the adherence to cells in the first regions 22 relatively high.

(3) A film which inhibits absorption of protein is formed on the second region 23, thereby making the adherence to cells in the second region 23 relatively low. Examples of material of the film include polyethylene glycol (PEG), 2-methacryloyloxyethyl phosphorylcholine (MPC), and the like.

(4) Minute projections may be formed in the second region 23 by surface treatment to decrease the area for cells to adhere, making the adherence to cells in the second region 23 relatively low.

Note that procedures of the method for measuring activity in another embodiment are mostly common to the first embodiment except that the microchamber sheet 21 is disposed in the culture container 13 and that the environmental factors are measured in each of the individual microchambers 14, and thus the description thereof is omitted. In addition, when alignment marks are provided in advance on the microchamber sheet 21 or the culture container 13, positioning becomes easy when the microchamber sheet 21 is disposed in the culture container 13.

According to another embodiment, in addition to the effects of one embodiment, measurement of activity of cells can be performed at once in arrays. Thus, throughput for evaluating activity of plural cells can be increased significantly. Further, in another embodiment, by having the arrays, it is unnecessary to align the individual microchambers 14 separately. Thus, complexity of measurement work decreases, and working efficiency improves further.

<Structure Example of a Device for Measuring Activity>

Figures 8, 9:
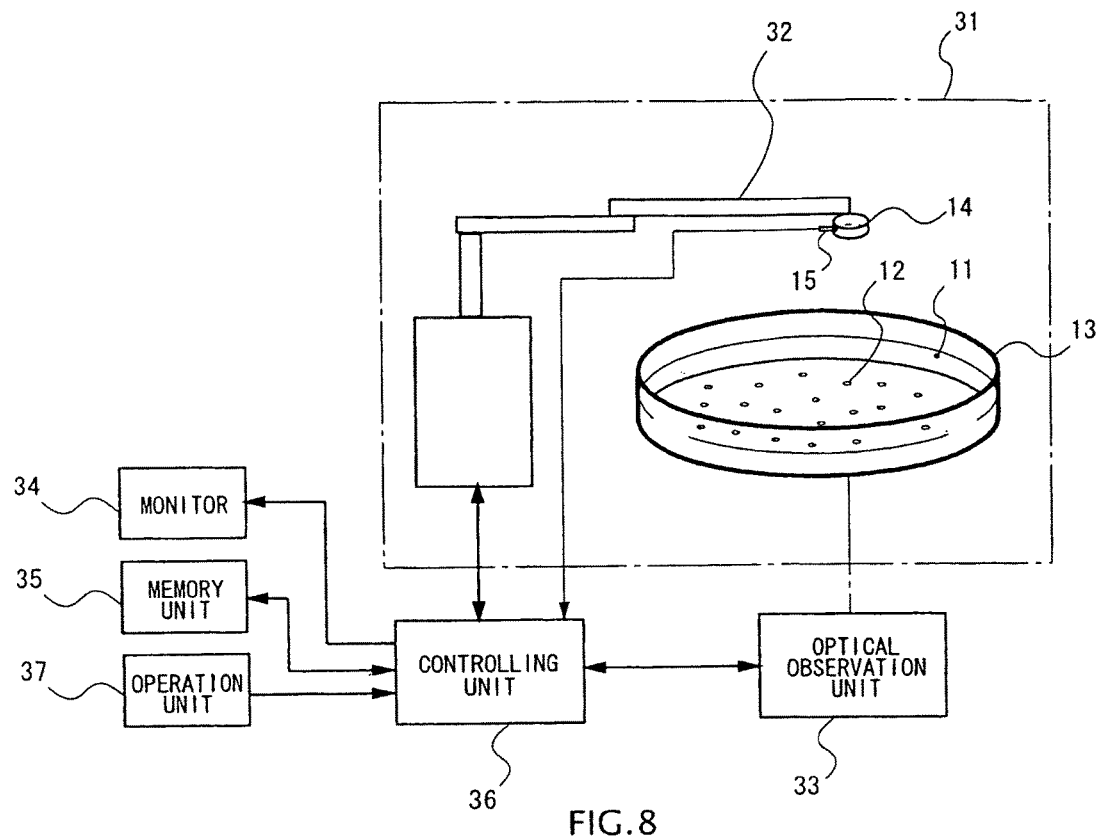
FIG. 8 is a block diagram illustrating a structure example of a device for measuring activity.
FIG. 9 is a flowchart illustrating an operation example of the device for measuring activity.

FIG. 8 is a block diagram illustrating a structure example of a device for measuring activity for carrying out the method for measuring activity of the above-described one embodiment or another embodiment.

The device for measuring activity has a temperature-controlled room 31, a robot arm 32, an optical observation unit 33, a monitor 34, a memory unit 35, a controlling unit 36, and an operation unit 37 accepting various operations from the user. Here, the robot arm 32, the optical observation unit 33, the monitor 34, the memory unit 35, and the operation unit 37 are connected to the controlling unit 36.

The temperature-controlled room 31 accommodates the culture container 13 in which cells 12 to be measured are incubated. Inside this temperature-controlled room 31, an environment suitable to incubation of cells (for example, an atmosphere at a temperature of 37° C. and at a humidity of 90%) is maintained, and high cleanliness is maintained for preventing contamination.

The robot arm 32 holds the microchamber 14 (or the microchamber sheet 21) on its front end, and moves the microchamber 14 three-dimensionally. In response to instructions from the controlling unit 36, the robot arm 32 performs operations to place the microchamber 14 to cover a cell 12 at a predetermined position in the culture container 13, and to remove the microchamber 14 after measurement is finished.

The optical observation unit 33 has an illumination device lighting cultured cells, a microscopic optical system for observing the cultured cells, and an imaging device imaging an object in the culture container 13 via the microscopic optical system. This optical observation unit 33 is used for obtaining position information when the robot arm 32 positions the microchamber 14 in the culture container 13, and for obtaining image information indicating an optical change occurring in the measurement space in the microchamber 14. Here, the image taken in the optical observation unit 33 can be displayed on the monitor 34 under control of the controlling unit 36.

The memory unit 35 is formed of a non-volatile storage medium such as a hard disk or a flash memory. In this memory unit 35, measurement information of the environmental factors and image information generated by the optical observation unit 33 during measurement of the environmental factors are stored. The image information and the measurement information of environmental factors are stored in the memory unit 35 in a state of being correlated with identification information of the cells to be measured and measurement date and time information. In the memory unit 35, a program to be executed by the controlling unit 36 is also stored.

The controlling unit 36 is a processor controlling operations of the respective parts of the device for measuring activity in a centralized manner. For example, the controlling unit 36 controls the robot arm 32 to move the microchamber 14. Further, the controlling unit 36 performs measurement of the environmental factors in the microchamber 14 with the imaging device of the optical observation unit 33 and the environmental factor sensor 15 in the microchamber 14.

Hereinafter, an operation example of the device for measuring activity will be described with reference to the flowchart of FIG. 9.

Step S101: the controlling unit 36 activates the optical observation unit 33 to obtain an observation image capturing the state in the culture container 13. Thus, the controlling unit 36 obtains the position information for positioning the microchamber 14. For example, the controlling unit 36 correlates a reference point of an image (for example, the center of an image) with a position in the culture container 13 in advance. Then the controlling unit 36 can geometrically obtain actual coordinates of a cell in the culture container 13 from the positional relationship between the cell in the image and the reference point, considering magnifying power, lens position, and so on in the optical observation unit 33.

Thereafter, the controlling unit 36 displays the aforementioned observation image on the monitor 34. Accordingly, the user can specify the cell 12 to be measured with the operation unit 37 based on the observation image.

Step S102: upon reception of the specification of the cell 12 to be measured from the user, the controlling unit 36 drives the robot arm 32 based on the aforementioned position information (S101) to dispose the microchamber 14 from an upper side of the cell 12 to be measured. Thus, the measurement space is formed by the microchamber 14 surrounding the cell 12 to be measured.

Step S103: the controlling unit 36 carries out measurement of the environmental factors in the measurement space by taking an image with the optical observation unit 33 and by outputs of the environmental factor sensor 15. After statistically analyzing measurement results of the environmental factors as necessary, the controlling unit 36 records the measurement results in the memory unit 35 and displays the measurement results on the monitor 34.

Step S104: after the measurement is completed, the controlling unit 36 drives the robot arm 32 to remove the microchamber 14 from the culture container 13, and recovers the incubating environment in the culture container 13.

Thus, the description of the flowchart of FIG. 9 is completed. Using the above-described device for measuring activity, it is possible to carry out the method for measuring activity of the above-described embodiment efficiently.

EXAMPLE

As an example, a calibration curve of an oxygen sensor was created, so as to demonstrate that measurement of a dissolved oxygen concentration in the microchamber (reactor) is possible.

Figure 10:
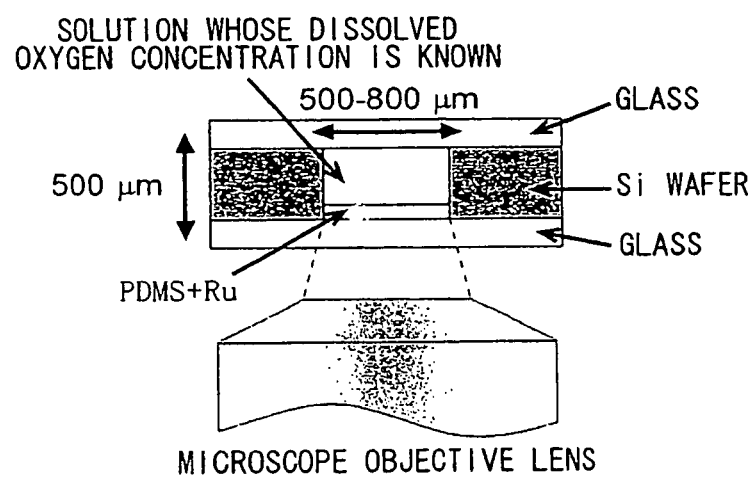
FIG. 10 is a schematic diagram illustrating the structure of a measurement system in an example.

FIG. 10 is a schematic diagram illustrating the structure of a measurement system in the example. In the example, a sheet of polydimethylsiloxane (PDMS) containing a ruthenium (Ru) complex is disposed on a glass substrate, and this glass substrate on which the aforementioned sheet is disposed and a silicon (Si) wafer in which a hole having a diameter of 500 μm to 800 μm is bored are bonded together to form a reactor. Further, an upper side of the Si wafer is enclosed with a glass substrate. Here, the thickness of the entire reactor is 500 μm.

Solutions having different dissolved oxygen concentrations were enclosed in the aforementioned reactor, and fluorescence intensity in each of them was measured with a microscope.

Figure 11:
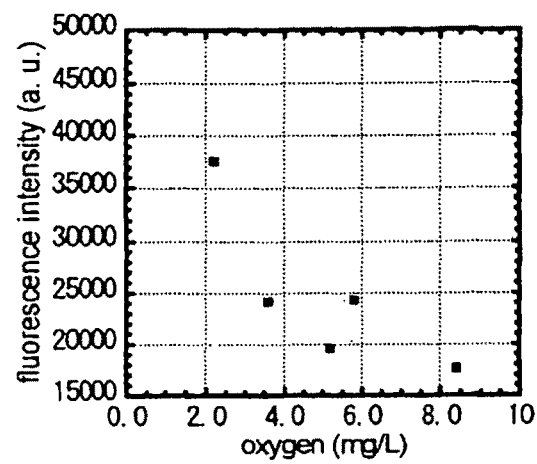
FIG. 11 is a graph illustrating a relation between fluorescence intensity and a dissolved oxygen concentration in the example.

FIG. 11 is a graph illustrating a relation between fluorescence intensity and a dissolved oxygen concentration in the example. From FIG. 11, it is recognized that the fluorescence intensity decreases as the dissolved oxygen concentration in the reactor increases.

Next, the calibration curve of the oxygen sensor is created based on experimental data from the example. A parameter of the calibration curve is represented with the following equation (1).

$$I_0/I = 1 + K_{SV}[O_2] \quad (1)$$

Here, "$I_0$" denotes the fluorescence intensity when the dissolved oxygen concentration is 0 mg/L. "I" denotes the fluorescence intensity with respect to each dissolved oxygen concentration. "$K_{SV}$" denotes a value indicating an inclination of the calibration curve. "$O_2$" denotes the dissolved oxygen concentration.

Figure 12:
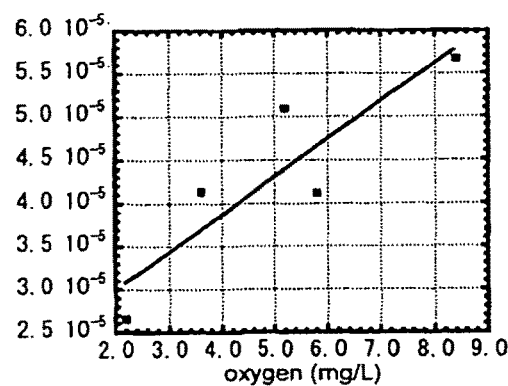
FIG. 12 is a graph illustrating a relation between an inverse number of the fluorescence intensity and the dissolved oxygen concentration in the example.

In the example, since the fluorescence intensity when the dissolved oxygen concentration is 0 mg/L cannot be obtained by experiment, the inverse number of the fluorescence intensity is approximated with a straight line (see FIG. 12), and I" obtained from an intercept y of an approximation curve is assumed as the $I_0$.

$$I'' = 1/(2.159 \times 10^{-5}) = 46317.74 \quad (2)$$

Figure 13:
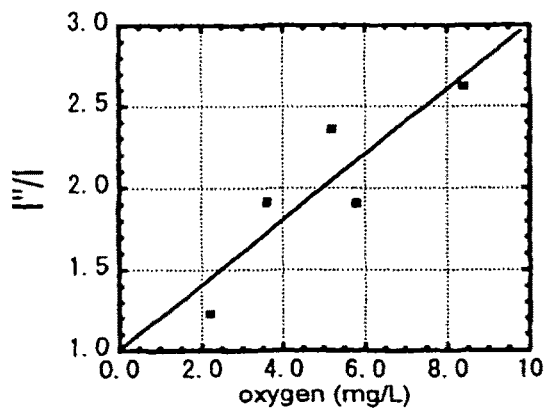
FIG. 13 is a graph illustrating a calibration curve in the example.

Using the aforementioned I", the calibration curve was created with a vertical axis being I"/I and a horizontal axis being the dissolved oxygen concentration (see FIG. 13). At this time, $K_{SV} = 0.19976$.

<Supplemental Items of the Embodiments>

(1) In the above-described embodiments, when a light curing resin is used for the microchamber 14, an arbitrary cell can be enclosed in the microchamber 14 by irradiating the microchamber 14 with laser. With this structure, it becomes possible to selectively separate and extract a desired cell based on measurement results of environmental factors in the measurement space.

(2) In the example of FIG. 4, an opening part covered with a hydrophobic semi-permeable film 17 may be formed on a side face of the microchamber 14.

(3) In the above-described embodiments, when fluorescence in the microchamber 14 is observed, a reflective film reflecting the wavelength of fluorescence may be formed on the inside of a side wall of the microchamber 14. With this structure, it becomes possible to detect a fluorescence signal in the microchamber 14 with higher sensitivity.

(4) In addition, it is preferred that the instruments of the above-described embodiments, such as the microchamber 14, the microchamber sheet 21, the culture container 13, and so on, be designed as a disposal item.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A microchamber sheet that is configured to be disposed in a culture container over a bottom face of the culture container, the microchamber sheet comprising:
    a sheet main body in which a plurality of cell accommodating units are arranged, wherein
        the sheet main body is configured such that an undersurface of the sheet main body faces toward the bottom face of the culture container when the microchamber sheet is disposed in the culture container,
        each of the cell accommodating units has a cylindrical shape, an upper side that is closed, and a lower side that is open,
        each of the cell accommodating units forms a measurement space which is sufficiently small with respect to a volume of the culture container and that is configured to cover a cell to be measured in the culture container when the microchamber sheet is disposed in the culture container, and
        each of the cell accommodating units includes an environmental factor sensor that measures an amount of an environmental factor surrounding the cell to be measured, the environmental factor sensor being: (i) fixed on the inside of the respective cell accommodating unit, and (ii) configured to generate an electrical signal.

2. The microchamber sheet according to claim 1, wherein an inner surface of each of the cell accommodating units is formed with a hydrophilic film.

3. The microchamber sheet according to claim 1, wherein the upper sides of each of the cell accommodating units is flat.

4. The microchamber sheet according to claim 1, wherein the upper side of each of the cell accommodating units is closed by being covered by a semi-permeable film that blocks a culture solution from flowing in or out.

5. The microchamber sheet according to claim 1, wherein each of the cell accommodating units includes a detecting probe that is: (i) fixed in an inner surface of the respective cell accommodating unit, and (ii) configured to indicate an optical change according to an amount of the environmental factor contained in a culture solution of the respective cell accommodating unit.

6. The microchamber sheet according to claim 1, wherein the microchamber sheet is formed of a translucent material.

7. The microchamber sheet according to claim 1, wherein the microchamber sheet is formed of an elastic material.

8. A device used in measuring activity of cultured cells, the device comprising:
    a culture container;
    a microchamber sheet that is configured to be disposed in the culture container over a bottom face of the culture container, and in which a plurality of cell accommodating units are formed in a bottom face of the microchamber sheet, each of the cell accommodating units being formed of a cylindrical recessed portion with a bottom, and having a cylindrical shape, an upper side that is closed, and a lower side that is open; and
    an optical observation unit configured to perform an observation of the cultured cells, wherein the sheet main body is configured such that an undersurface of the sheet main body faces toward the bottom face of the culture container when the microchamber sheet is disposed in the culture container, each of the cell accommodating units forms a measurement space which is sufficiently small with respect to a volume of the culture container and that is configured to cover a cell to be measured in the culture container when the microchamber sheet is disposed in the culture container, and each of the cell accommodating units includes at least one of: (i) an environmental factor sensor that measures an amount of an environmental factor surrounding the cell to be measured, and (ii) a detecting probe that optically-indicates an intensity of target molecules having the environmental factor surrounding the cell to be measured, the environmental factor sensor being: (i) fixed on the inside of the respective cell accommodating unit, and (ii) configured to generate an electrical signal.

9. A method for measuring activity of cultured cells comprising:

disposing the microchamber sheet according to claim 1 in the culture container such that each of the cell accommodating units surrounds a cell to be measured;

measuring environmental factors contained in the measurement spaces formed by each of the cell accommodating units; and removing the microchamber sheet from the culture container when the measuring is finished.

10. The microchamber sheet according to claim 1, wherein the bottom face of the culture container, when the microchamber sheet is disposed in the culture container, delimits the lower boundary of the measurement space surrounding the cell to be measured.

11. The device according to claim 8, wherein the bottom face of the culture container, when the microchamber sheet is disposed in the culture container, delimits the lower boundary of the measurement space surrounding the cell to be measured.

12. The microchamber sheet according to claim 1, wherein the bottom face of the culture container has an array of attached cells.

13. The device according to claim 8, wherein the bottom face of the culture container has an array of attached cells.

14. The microchamber sheet according to claim 1, wherein the environmental factor sensor fixed in the inner surface of each of the cell accommodating units is an oxygen sensor.

15. The device according to claim 8, wherein the environmental factor sensor fixed in the inner surface of each of the cell accommodating units is an oxygen sensor.

16. The device according to claim 8, wherein the at least one of the environmental factor sensor, and the detecting probe includes a detecting probe that is: (i) fixed in an inner surface of the respective cell accommodating unit, and (ii) configured to indicate an optical change according to an amount of the environmental factor contained in a culture solution of the respective cell accommodating unit.

17. The microchamber sheet according to claim 1, wherein each of the cell accommodating units includes a detecting probe that optically-indicates an intensity of target molecules having the environmental factor surrounding the cell to be measured.

18. The microchamber sheet according to claim 1, wherein each of the cell accommodating units further comprises a microlens formed on an upper surface of the respective cell accommodating unit.

19. The device according to claim 8, further comprising: a robot arm which disposes the microchamber sheet inside the culture container before a measurement, and removes the microchamber sheet from the culture container after the measurement.

* * * * *